United States Patent [19]
Malata, Jr.

[11] Patent Number: 5,090,905
[45] Date of Patent: Feb. 25, 1992

[54] ENDODONTIC FILING TOOL

[75] Inventor: Peter Malata, Jr., Bürmoos, Austria

[73] Assignee: Dentalwerk Bürmoos Gesellschaft m.b.H, Bürmoos, Austria

[21] Appl. No.: 541,917

[22] Filed: Jun. 21, 1990

[51] Int. Cl.⁵ ............................. A61C 5/02; A61C 1/14
[52] U.S. Cl. .................................... 433/102; 433/128
[58] Field of Search ............... 433/102, 141, 146, 147, 433/165, 128, 127

[56] References Cited

U.S. PATENT DOCUMENTS

| | | | |
|---|---|---|---|
| 2,715,772 | 8/1955 | Fritz | 433/165 |
| 4,019,254 | 4/1977 | Malmin | 433/102 |
| 4,940,410 | 7/1990 | Apap et al. | 433/102 |
| 5,028,181 | 7/1991 | Jenkins et al. | 409/215 |

FOREIGN PATENT DOCUMENTS 720228 12/1954 United Kingdom .............. 433/141

*Primary Examiner*—John J. Wilson
*Assistant Examiner*—Cindy A. Cherichetti
*Attorney, Agent, or Firm*—Toren, McGeady & Associates

[57] ABSTRACT

An endodontic filing tool which can be chucked into a dental tool holder with slight play but secured against rotating movement as well as against axial movement by chucking balls. A circumferential groove is provided at the rearward end of the tool shaft, wherein the circumferential groove is interrupted at at least one location, so that a stop for the chucking ball is formed.

3 Claims, 1 Drawing Sheet

ENDODONTIC FILING TOOL

BACKGROUND OF THE INVENTION

1. Field of the Invention

The present invention relates to an endodontic filing tool which can be mounted with a slight play in a dental tool holder while being secured against rotation as well as against axial movement.

2. Description of the Related Art

A tool and tool holder of the above-described type are known from Austrian patent 388,283. The content of this Austrian patent is incorporated herein by reference. In order to hold the tool in the tool holder, the Austrian patent 388,283 provides that the rearward end of the shaft of the tool has at least one spherically-shaped recess and at least one chucking ball is provided in the tool holder, wherein the chucking ball is pressed radially inwardly into the spherically-shaped recess by means of a spring. The spring does not have to act directly against the ball; rather, particularly when several balls are provided, a force-transmitting structural component may be provided.

The tool holding machanism described above operates as required, however, the mechanism is difficult to manufacture because the spherically-shaped recesses can only be manufactured by means of high precison tools and the assembly of the tool requires a careful and sensitive treatment in order to engage the ball or balls in the recess or recesses.

SUMMARY OF THE INVENTION

It is, therefore, the primary object of the present invention to provide a tool holding mechanism which has the same properties in operation as the known holding mechanism, however, is simpler to assemble and less expensive to manufacture.

In accordance with the present invention, this object is met by providing a circumferential groove at the rearward end of the tool shaft, wherein the circumferential groove is interrupted at at least one location.

The groove provided in accordance with the invention can be manufactured inexpensively and without problems by means of grinding or cutting tools. Surprisingly, the at least one interruption of the groove is completely sufficient for securing the filing tool against a rotating movement. When the tool holder is used, a wobbling movement is imparted to the end of the tool shaft on the side of the file. This wobbling movement applies a small torque to the tool shaft. This torque may be changeable, but does not change its direction. The torque causes the tool shaft to be rotated to the stop, i.e., to the interruption of the groove, before the tool comes into contact with the patient.

The rotation is dependent upon the angular position of the tool shaft when it is inserted. However, the rotation is always less than 360°. When two interruptions of the groove are provided, the rotation is smaller than 180° and occurs within a very short time. Consequently, the applied torque results in the stop resting against the chucking ball, so that the tool holder is secured against rotation.

The holding mechanism of the file in accordance with the present invention leads to surprisingly improved results in operating the file:

Most files which are used are made from twisted metal wires with polygonal cross-sections or from almost round wires with filing elements which are arranged on the wire surface along helical lines. Due to the axial movement of the file obtained during the use through the movement of the instrument, alternating moments are exerted on the filing tool as a result of the shape of the file, wherein the alternating moments are superimposed on the driving moment.

These effects have not yet been evaluated in detail, however, it is suspected that they may cause a reversal of the moments acting on the file and cause an improvement in the operation the file if the file can follow the moments, as in the tool according to the invention.

The use of the tool according to the invention is substantially simpler than the use of the known tool because there exists practically only a narrowly limited angular position of the tool in which the ball or balls cannot be engaged. By a slight rotation of the tool, it is always possible without problems to place the chucking ball or balls in the groove because it is not possible to "jump" over the spherically-shaped recesses.

The various features of novelty which characterize the invention are pointed out with particularity in the claims annexed to and forming a part of this disclosure. For a better understanding of the invention, its operating advantages and specific objects attained by its use, reference should be had to the drawing and descriptive matter in which there is illustrated and described a preferred embodiment of the invention.

DESCRIPTION OF THE PREFERRED EMBODIMENT

Figure 1:
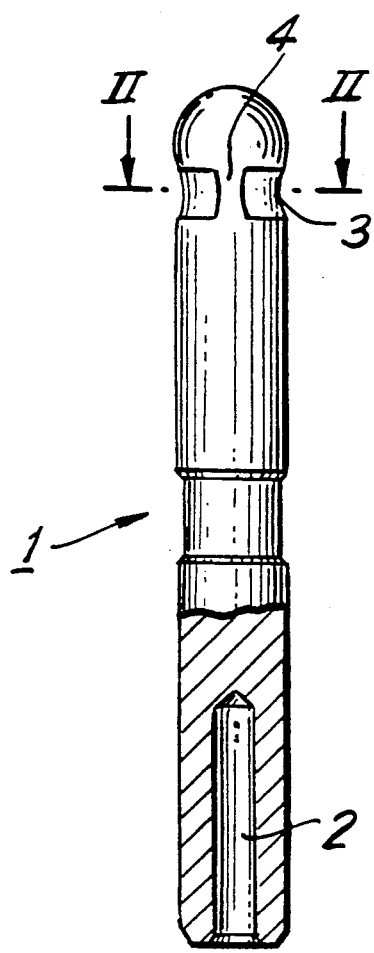
FIG. 1 is a view, partially in section, of the tool shaft according to the present invention.

FIG. 1 of the drawing shows a tool support member 1, partially in section. At the end of the tool support member 1 on the side of the tool is provided a central coaxial bore 2 for receiving the actual tool. At the end facing away from the tool, a circumferential groove 3 is provided in the outer surface of the cylindrical support member. In the illustrated embodiment, the circumferential groove 3 is interrupted at two locations 4. These interruptions form stops for the chucking balls, not shown, of the dental tool holder which, when the tool support member is inserted in the tool holder so as to be ready for operation, extend under the action of a spring into the groove 2 and secure the tool support member against axial displacement and against rotation beyond the stop.

In the illustrated preferred embodiment, two stops 4 are provided in order to obtain a symmetrical mass distribution.

In the illustrated embodiment, the groove has a circular cross-section, wherein the diameter of the circle of the groove coincides with the diameter of chucking balls of the tool holder. However, this is not necessary; a different diameter or a different shape can also be provided. To avoid wear and for reasons of support, the illustrated shape is preferred and it is also preferred that the dimensions of groove and ball coincide.

It is not necessary that the tool support member and the tool are constructed in two pieces. Rather, it is possible to provide the shaft of single-piece tools with the recess according to the present invention, so that they can be used in the tool holders of the above-described type.

Figure 2:
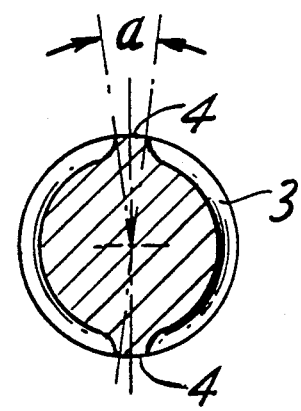
FIG. 2 is a sectional view taken along sectional line II—II of FIG. 1.

As can be seen from FIG. 2, when the tool or tool support member is inserted, almost the entire range of the possible angular positions between the tool support member and the tool holder is available. In the illustrated embodiment, the angle a included by the stop is 15° and, thus, is smaller than 10% of the possible insertion angle. Accordingly, a completely blind and random insertion will be successful in more than 90% of the cases, while the remaining approximately 7% require a slight rotation of the tool support member in the tool holder. However, in reality, the insertion of the tool support member is not random but takes place at an angular position which is recognized as being approximately correct. Since, according to the invention, a very large angular range is available, a completely problem-free insertion of the tool is ensured in daily operation.

In addition, compared to the known tool holding mechanisms, the rotation of the tool according to the present invention can be carried out much more easily because the construction of the circumferential groove does not render the angle of rotation critical. In the known tool holding mechanisms, it could easily happen that the tool support member was rotated beyond a locking position and that at the end of the rotating movement, the chucking balls were again resting against the tool support member shaft outside of the spherically-shaped recesses without resulting in the necessary locking action.

Moreover, it is possible to reduce the width of the stop. It is even possible to keep the width of the stop so small that the stop no longer completely extends to the cylindrical surface of the tool support member. The rotation has thus been further facilitated because of the resulting sharp edge extending in the region of a generatrix of the surface of the tool support member. It must only be ensured that the influence of the torque which is transmitted by the wobbling tool cannot cause the chucking ball or balls to jump over the remaining stop.

It is also possible to divide the circumferential groove not only at one or two locations, but at three or four locations. However, an interruption at two locations is preferred for the above-described reasons, namely, the simplified and less expensive manufacture, the simplified insertion in the tool holder and the desired mass compensation.

While a specific embodiment of the invention has been shown and described in detail to illustrate the application of the inventive principles, it will be understood that the invention may be embodied otherwise without departing from such principles.

I claim:

1. In an endodontic filing tool having a tool shaft with a rearward end, the tool shaft having a circular cross-section, the filing tool being chucked in a dental tool holder with slight play by means of chucking balls, but being secured against rotation as well as against axial movement, the improvement comprising the tool shaft having at the rearward end thereof a circumferential groove receiving the chucking balls, the circumferential groove having an interruption at at least one location, such that the interruption forms a stop for the chucking balls.

2. The filing tool according to claim 1, wherein the circumferential groove is interrupted at two locations.

3. The filing tool according to claim 1, wherein the circumferential groove has a circular cross-section.

* * * * *